(12) United States Patent
Perry

(10) Patent No.: US 8,597,207 B1
(45) Date of Patent: Dec. 3, 2013

(54) URINE COLLECTION APPARATUS

(76) Inventor: Robert J. Perry, Oklahoma City, OK (US)

( * ) Notice: Subject to any disclaimer, the term of this patent is extended or adjusted under 35 U.S.C. 154(b) by 90 days.

(21) Appl. No.: 12/425,181

(22) Filed: Apr. 16, 2009

Related U.S. Application Data

(60) Provisional application No. 61/045,401, filed on Apr. 16, 2008.

(51) Int. Cl.
*A61B 5/00* (2006.01)

(52) U.S. Cl.
USPC .......................................................... 600/574

(58) Field of Classification Search
USPC ................ 144/331, 332, 337; 4/144.1, 144.4; 600/573, 574, 584; 604/317, 329, 347
See application file for complete search history.

(56) References Cited

U.S. PATENT DOCUMENTS

| | | | | |
|---|---|---|---|---|
| 3,161,891 A | * | 12/1964 | Bauman | 600/574 |
| 3,625,654 A | * | 12/1971 | Van Duyne | 600/574 |
| 3,811,136 A | * | 5/1974 | Whitney et al. | 600/573 |
| 3,832,738 A | * | 9/1974 | Kliemann | 4/144.1 |
| 4,106,490 A | * | 8/1978 | Spilman et al. | 600/574 |
| 4,335,730 A | * | 6/1982 | Griffin | 600/573 |
| 5,422,076 A | * | 6/1995 | Jones | 600/574 |
| 6,299,606 B1 | * | 10/2001 | Young | 604/329 |
| D456,898 S | | 5/2002 | Yang | |
| 6,409,971 B1 | * | 6/2002 | Wilkinson et al. | 422/537 |
| 6,651,259 B1 | * | 11/2003 | Hartman et al. | 4/144.1 |
| 6,908,441 B1 | * | 6/2005 | Bernard et al. | 600/574 |
| 2002/0179794 A1 | | 12/2002 | Yang | |
| 2006/0149164 A1 | * | 7/2006 | Lee et al. | 600/573 |
| 2006/0184064 A1 | * | 8/2006 | Paasch et al. | 600/573 |

* cited by examiner

*Primary Examiner* — Max Hindenburg
(74) *Attorney, Agent, or Firm* — San Diego IP Law Group, LLP

(57) ABSTRACT

A urine collection apparatus that includes at least a handle providing a contoured rim portion that is configured to conform to female genitals. Preferably, a urine collection port is offset from the rim portion. The preferred embodiment further includes a sloped surface disposed between the urine collection port and the rim portion, and wherein the rim portion presents a length, at its greatest extent, that is more than twice its width at the width's greatest extent.

2 Claims, 6 Drawing Sheets

URINE COLLECTION APPARATUS

RELATED APPLICATIONS

This application claims domestic priority to U.S. Provisional Application No. 61/045,401 filed Apr. 16, 2008, entitled "Urine Collection Apparatus."

FIELD OF THE INVENTION

The present invention relates generally to the collection of female urine, but not by way of limitation, to the field of medical equipment.

BACKGROUND OF THE INVENTION

The ability to safely and efficiently collect female urine has been a continued goal of various industries such as medical, camping, and recreation.

Historically, medical urine collection has been carried out by manually inserting a sterile sample cup into a urine stream for a small period of time. The manual insertion of a sample cup into a urine stream creates a potential for contamination by the urine touching the hand on its way to the sample cup. Likewise, manual insertion of the sample cup into a urine stream often results in lost urine due to the lack of a convenient line of sight for females. The integrity of the urine sample is further endangered when a user gets urine on the outside of the sample cup that must be absorbed by a potentially non-sterile material by a medical technician. The ability to efficiently collect urine without getting fluid on the outside of the sample cup greatly increases the chances of the sample having the proper integrity. Similarly, efficient collection of a urine sample without the possibility of getting fluid on the outside of the sample cup greatly decreases the time required to collect the sample as well as the time the sample will be uncovered in the cup.

In addition, the efficient and safe collection of urine has been an issue for the camping and recreation industries because of the inability for females to conveniently supervise the urination process. At times when plumbing is not available such as on a boat or camping, females often cannot conveniently control urination. Thus, an apparatus that allows a female to isolate their urine stream into a specified location without having to squat close to the ground will greatly increase the efficiency and safety of urinating without plumbing.

Many attempts have been made to provide a urine collection appliance to collect urine samples including U.S. Design Pat. No. D456,898 and U.S. Patent Application No. 2002/0179794. However, none of the disclosed appliances provide an efficient and safe method of collecting a sample with minimal possibility of sample contamination. The U.S. Design Pat. No. D456,898 discloses a sample cup holder that connects to a toilet stool. However, this design does not account for the variations in user size as well as the lack of efficient line of sight to supervise the filling of the cup. While the design takes the user's hand out of the process, the appliance remains inefficient with a high potential for sample contamination. Moreover, U.S. Patent Application No. 2002/0179794 is an adjustable sample cup holder connectable to a toilet stool. The adjustability of the disclosed appliance allows for a variety of positions for the sample cup, however, the user is required to awkwardly find a line of sight to ensure the cup is filled with the proper amount of urine. Therefore, attempts have been made to make the collection of a urine sample more efficient and safe, but have failed to provide an appliance that allows the user a time efficient sterile process.

Furthermore, the requirement that both references have a toilet stool to hold a sample cup is evidence of their ineffectiveness in locations that do not have plumbing. Areas such as campgrounds and boats often lack the required toilet stool which makes the cited references inefficient.

Accordingly, there is a continuing need for improved appliances to collect urine.

SUMMARY OF THE INVENTION

In accordance with the preferred embodiments, a urine collection apparatus that includes at least a handle. The handle provides a contoured rim portion that is configured to conform to female genitalia. In a preferred embodiment, a urine collection port is offset from the rim portion. A sloped surface is disposed between the rim portion and the urine collection port. Further in a preferred embodiment, a length of the rim portion at its greatest extent is greater than twice a width of the rim portion at its greatest extent. In an alternate embodiment, a threaded means is provided in the urine collection port.

These and various other features and advantages which characterize the claimed invention will be apparent from reading the following detailed description and a review of the associated drawings

DETAILED DESCRIPTION OF THE INVENTION

Preferred embodiments of the present invention are generally directed to a urine collection apparatus configured to facilitate female urine collection.

Figure 1:
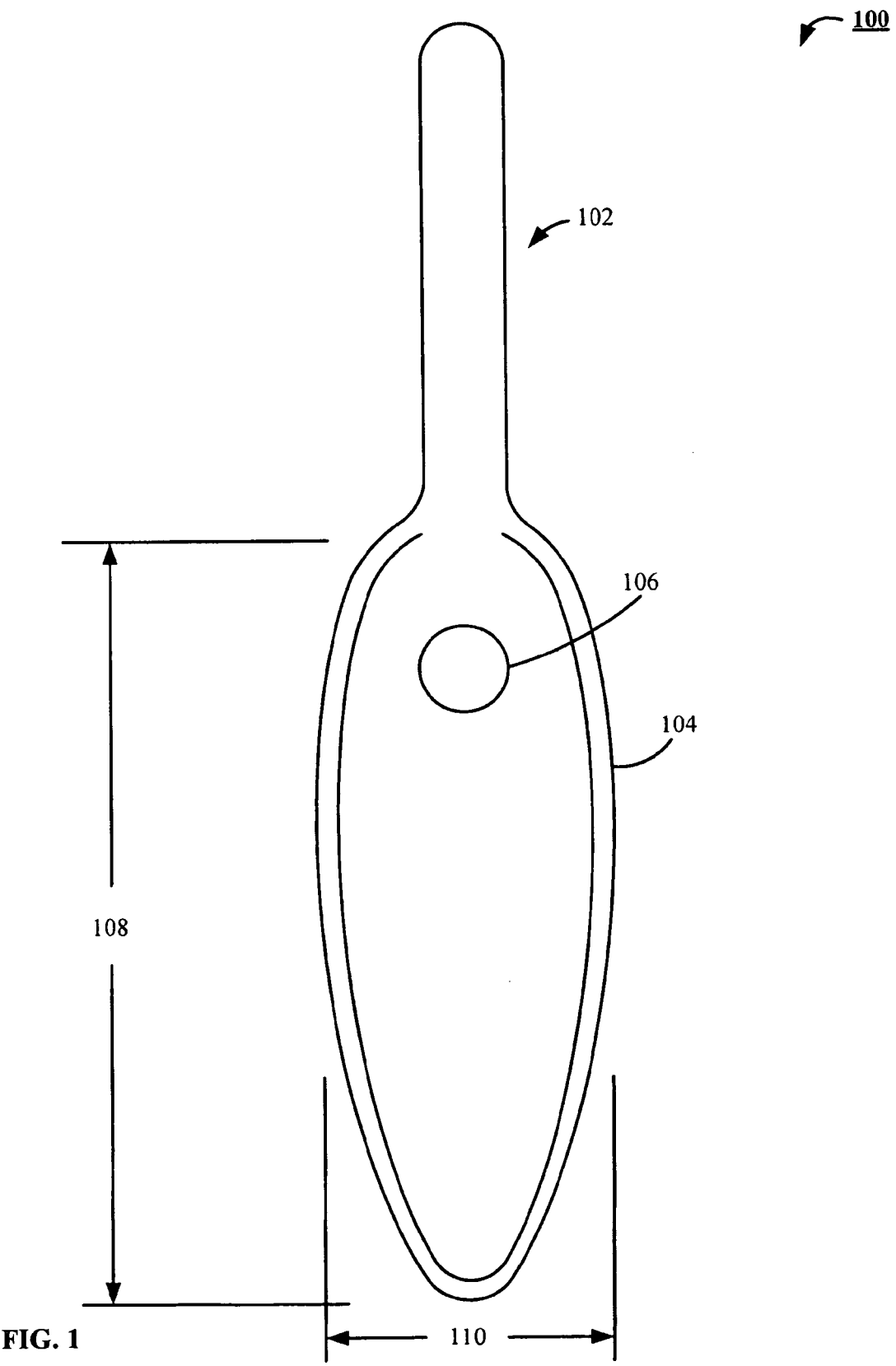
FIG. 1 is a top plan view of the urine collection apparatus in a preferred embodiment.

FIG. 1 shows a top plan view of the urine collection apparatus 100 in a preferred embodiment. The urine collection apparatus 100 preferably includes a handle 102 that provides a contoured rim portion 104, and a grip portion 105, the rim portion 104 is preferably configured to conform to the shape of female genitalia, and is preferably formed form a polymer such as polypropylene or a bioplastic, but may be formed from other material such as paper, metal, composite, ceramic, or other selected material. The rim portion 104 and handle 102 are preferably shaped to allow a female to grip the grip portion 105 and place the urine collection apparatus 100 between the legs of a user while standing upright, or seated, so that the rim portion 104 operatively surrounds the female genitalia and allows the user to conveniently isolate the destination of a urine stream. In a preferred embodiment, the urine collection apparatus 100 includes a urine collection port 106 that is offset from the rim portion 104. The urine collection port 106 can be offset from the rim portion 104 on either or both the vertical and horizontal axis. Further in a preferred embodiment, a sloped surface is disposed between the rim portion 104 and the urine collection port 106 to operatively funnel fluid to the urine collection port 106. A length of the rim portion 104 at its greatest extent 108 is preferably greater than twice the width of the rim portion 104 at its greatest extent 110.

Figure 2:
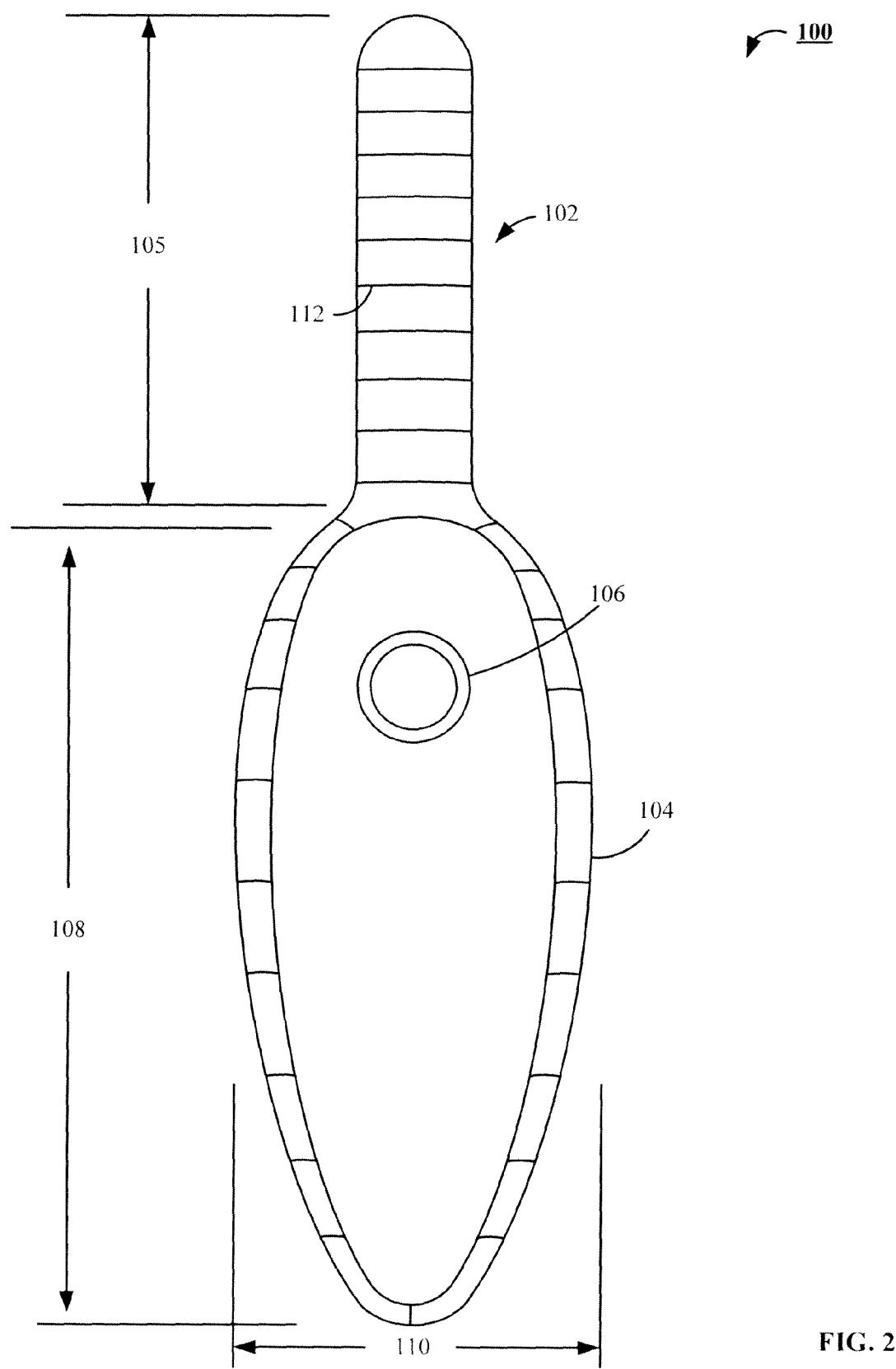
FIG. 2 is a bottom plan view of the urine collection apparatus in a preferred embodiment.

FIG. 2 displays a bottom plan view of the urine collection apparatus 100 in a preferred embodiment. The urine collection apparatus 100 includes a handle 102 and a urine collection port 106 that is offset from a rim portion 104. Preferably, a sloped surface is disposed between the rim portion 104 and the urine collection port. In a preferred embodiment, the rim portion 104 is rolled away from the urine collection port 106 so that the sloped surface continues over the rim portion 104. The rolled rim portion 104 provides no sharp edges that could irritate the gentle skin around the female genitals. The rolled rim portion 104 preferably includes a webbing member 112 that provides structural support for the rim 104 while providing a smooth rim portion.

Figure 3:
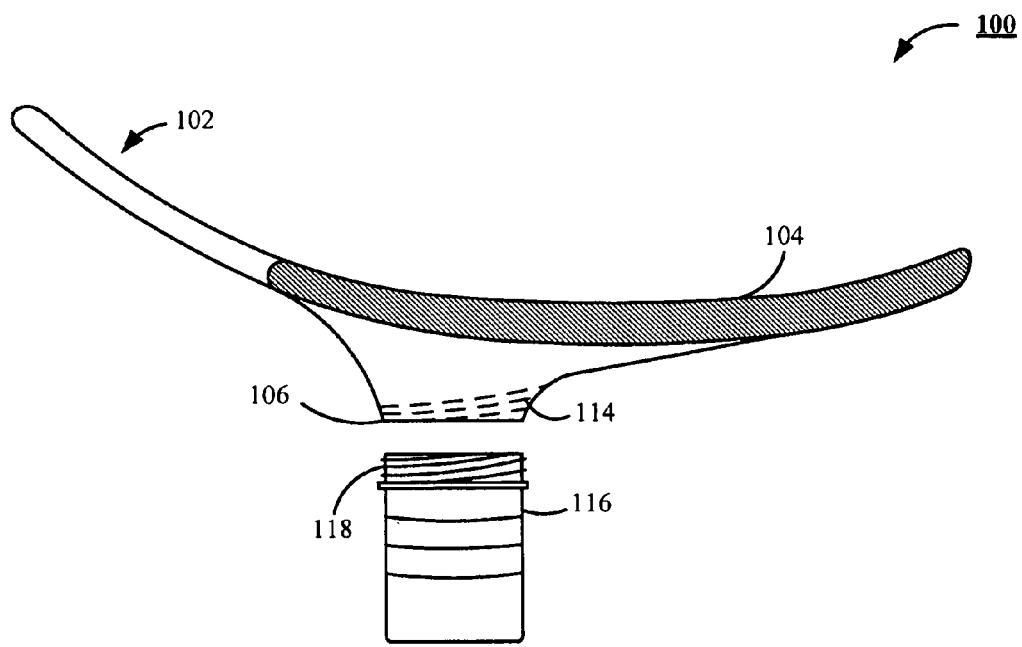
FIG. 3 is an exploded side elevation view of the urine collection apparatus in an alternate embodiment.

The illustration of FIG. 3 shows is an exploded side view of the urine collection apparatus 100 in an alternate embodiment. A handle 102 provides a contoured rim portion 104 that is configured to conform to the shape of female genitals. A sloped surface is preferably disposed between an offset urine collection port 106 and the rim portion 104. In an alternate embodiment, the urine collection port 106 includes a threaded connection means 114 that allows a union to an external reservoir such as a specimen cup 116, which preferably provides a threaded portion 118.

Figure 4:
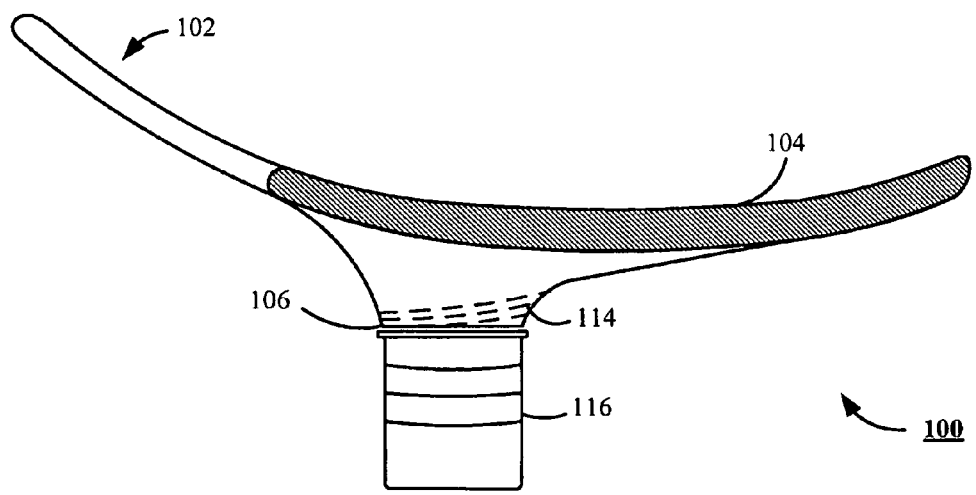
FIG. 4 is a side elevation view of the urine collection apparatus in an alternate embodiment.

The side plan view of the urine collection apparatus 100 in an alternate embodiment is displayed in FIG. 4. The handle 102 is shown providing a rim portion 104 that has an offset urine collection port 106. A sloped surface is preferably disposed between the rim portion 104 and the urine collection port 106. In an alternate embodiment, the urine collection port 106 includes the threaded connection means 114 that allows the specimen cup 116 to be attached in a watertight manner. Further, as shown by FIG. 3, the specimen cup 116 provides the threaded portion 118, which can be operatively joined to the threaded connection means 114.

Figure 5:
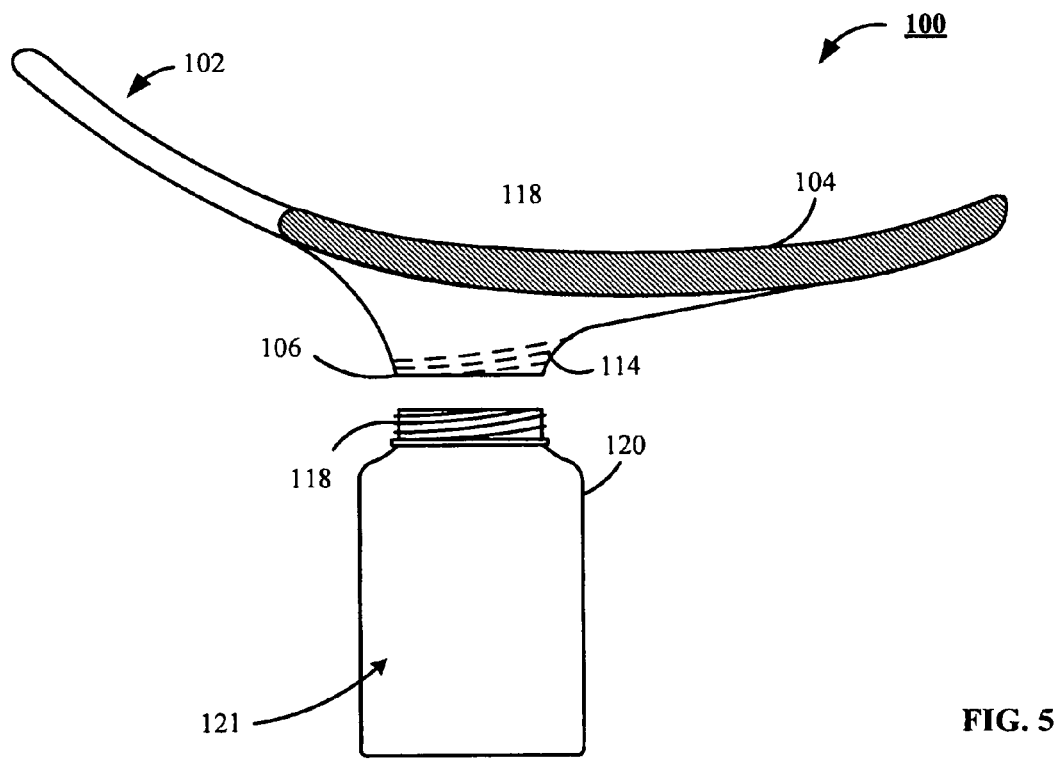
FIG. 5 is a side elevation view of the urine collection apparatus in an alternate embodiment.

FIG. 5 displays a side elevation view of the urine collection apparatus 100 in an alternate embodiment. The handle 102 provides the contoured rim portion 104 configured to conform to the shape of female genitals. A sloped surface is preferably disposed between the offset urine collection port 106 and the rim portion 104. In the present embodiment, the urine collection port 106 includes the threaded connection means 114 that allows a union to a urine transport means that has a threaded portion 118 communicating with a bottle 120, wherein the bottle 120 provides a volume 121 sized to collect all the urine produced during a single urination event.

Figure 6:
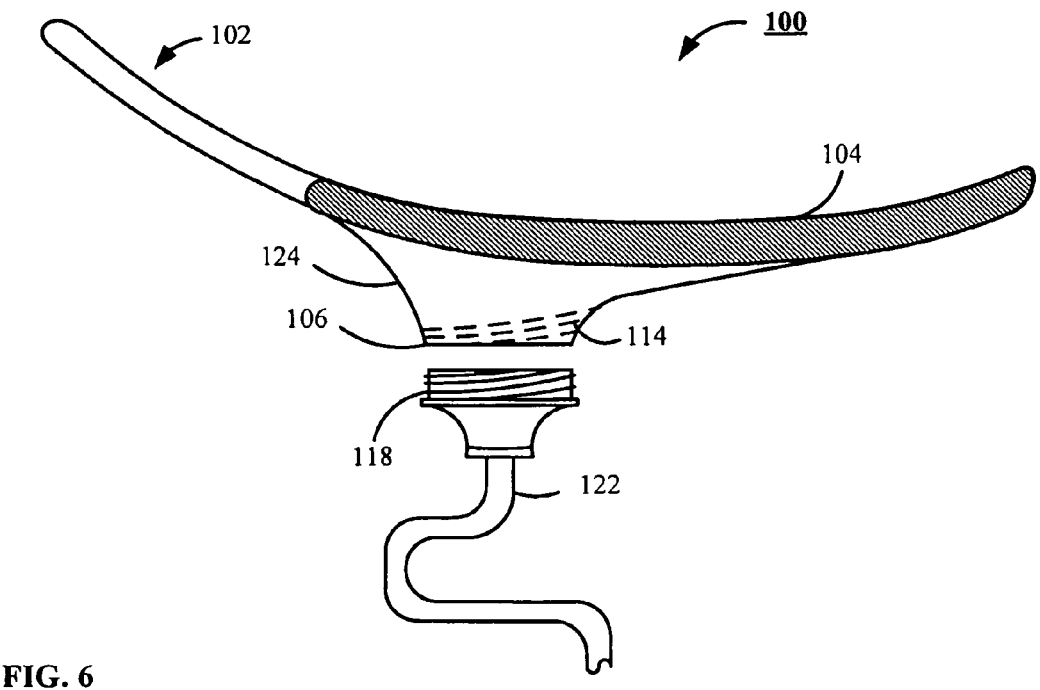
FIG. 6 is a side elevation view of the urine collection apparatus in an alternate embodiment.

The illustration of FIG. 6 shows the urine collection apparatus 100 in an alternate embodiment that includes a handle 102 providing the rim portion 104, and the offset urine collection port 106. A sloped surface is preferably disposed between the rim portion 104 and the urine collection port 106. The urine collection port 106 includes a threaded connection means 114 that allows a urine transport means to be attached in a watertight manner. The watertight connection can be to a wide range of disposal means which have a threaded portion 118 including, but not limited to, an evacuation tube 122

Figure 7:
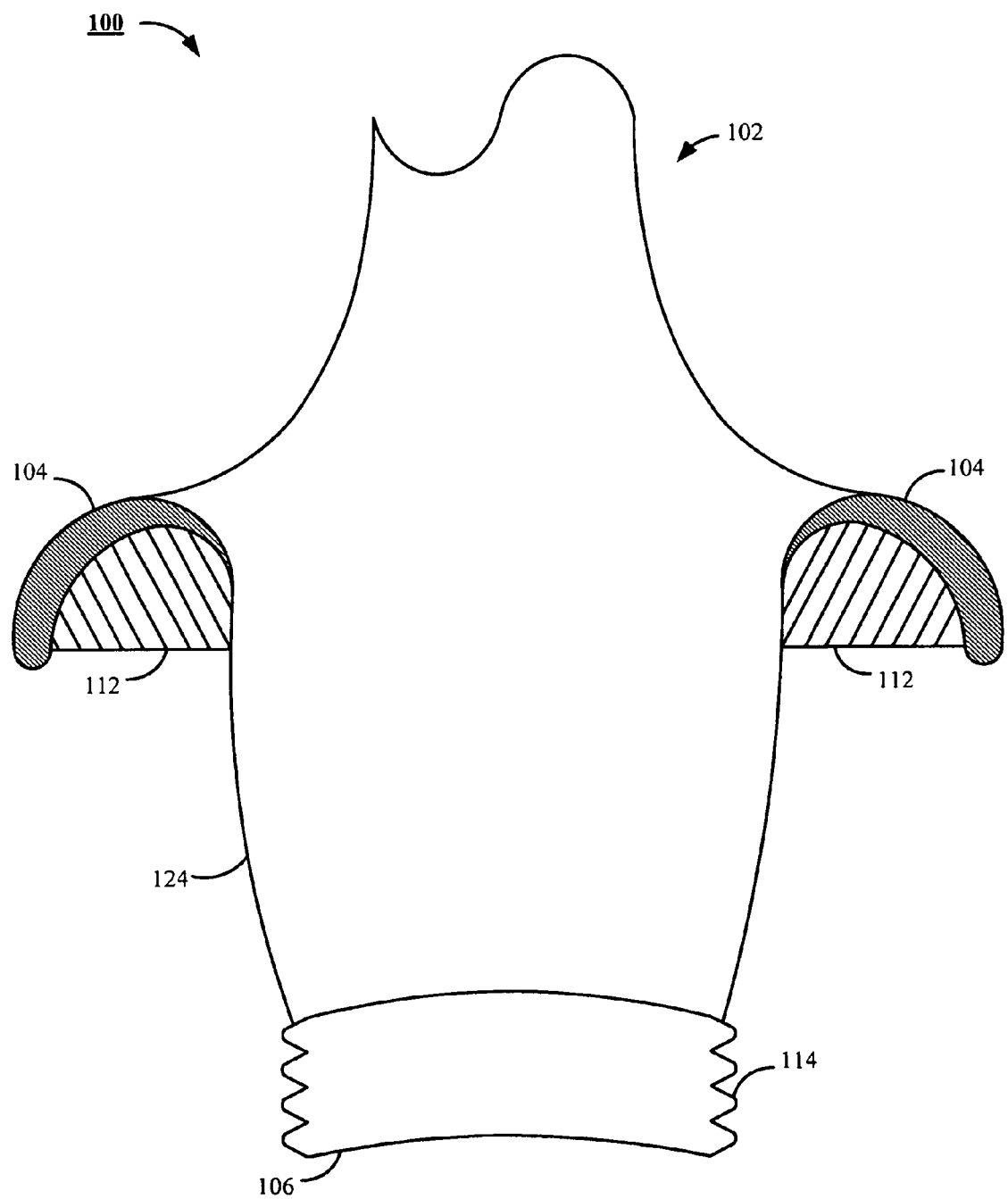
FIG. 7 is a partial cross-section view of the urine collection apparatus in a preferred embodiment.

The urine collection apparatus 100 of FIG. 7 shows the handle 102 providing a rim portion 104 supported by at least one webbing member 112 while providing a smooth top surface to contact female genitals. The urine collection port 106 is preferably offset from the rim portion 104, and communicates with the rim portion 104 via a sloped surface 124 disposed between the rim portion 104 and the urine collection port 106. Preferably, the urine collection port 106 includes the threaded connection means 114 that allows a urine transport means to be joined in a watertight manner.

Figure 8:
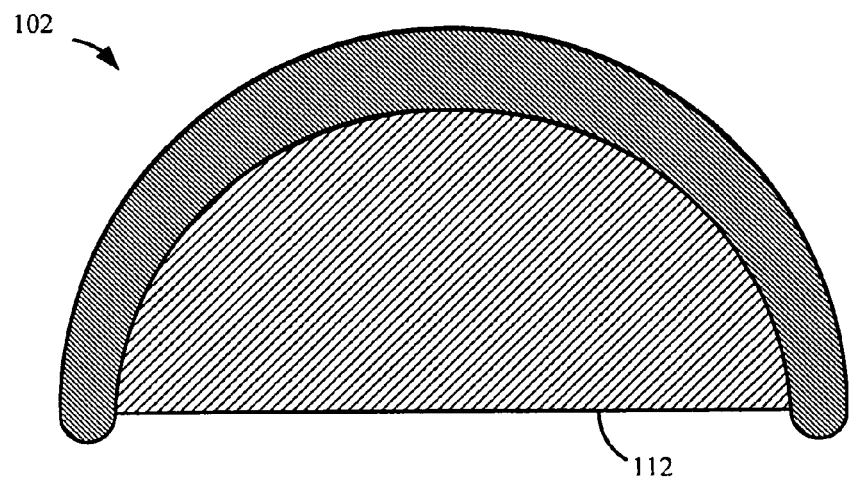
FIG. 8 is a partial cross-section view of the handle portion of the urine collection apparatus in a preferred embodiment.

FIG. 8 shows the handle 102 preferably presenting a predominantly rounded external surface to allow convenient and efficient grasping of the urine collection apparatus 100. Further in a preferred embodiment, a webbing member 112 spans the space below the curved handle to provide structural support.

Figure 9:
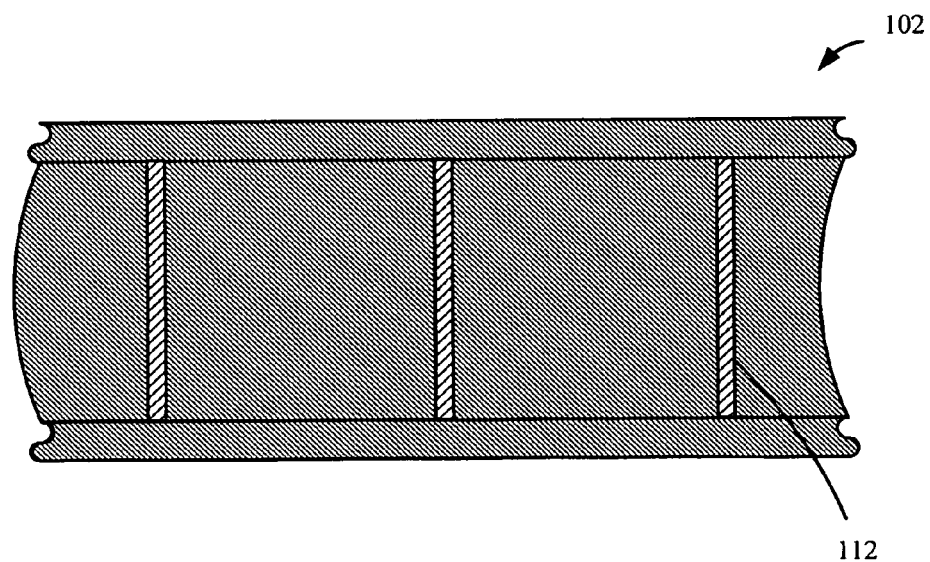
FIG. 9 is a partial cut-away bottom plan view of the handle of the urine collection apparatus in a preferred embodiment.

FIG. 9 shows the handle 102 of the urine collection apparatus 100 in a preferred embodiment. The handle 102 preferably includes a series of spaced apart webbing members 112 that provide structural support to the handle 102. The webbing members 112 can alternatively be configured to span only a portion of the space below the handle 102.

It will be clear that the present invention is well adapted to attain the ends and advantages mentioned as well as those inherent therein. While presently preferred embodiments have been described for purposes of this disclosure, numerous changes may be made which will readily suggest themselves to those skilled in the art and which are encompassed by the appended claims.

What is claimed is:

1. A method of using a urine collection apparatus, comprising:

providing a handle comprising a grip portion, a rim portion, and a webbing member, wherein the rim portion comprises a rolled rim portion, wherein the rolled rim portion curves downward to form a concave surface configured to allow a user to grip an underside of the rolled rim portion, wherein the webbing member extends from the underside of the rolled rim portion and extends from an underside of the grip portion, wherein the webbing member is configured to provide a grip for a user and configured to provide structural support to the underside of the rolled rim portion and to the underside of the grip portion;

gripping the webbing member of the handle, wherein rim portion has a length at its greatest extent that is more than twice the width of the rim portion at its greatest extent;

the grip portion having a length at its greatest extent not less than the width of the rim portion at the rim portion's greatest extent of width;

placing the rim portion to operatively surround a female's genitals; and directing urine to a urine collection port offset from a center of the rim portion by a sloped surface disposed between the rim portion and the urine collection port.

2. The method of claim 1, in which the grip portion further having a width at its greatest extent of width less than the width of the rim portion at the rim portion's greatest extend of width, and further comprising a step of securing a urine transport means to the urine collection port.

* * * * *